(12) United States Patent
Richards et al.

(10) Patent No.: US 9,411,013 B2
(45) Date of Patent: Aug. 9, 2016

(54) INSTRUMENT FOR AUTOMATED TESTING OF DISPLAYS

(71) Applicant: Google Inc., Mountain View, CA (US)

(72) Inventors: Evan M. Richards, Santa Clara, CA (US); Anurag Gupta, San Jose, CA (US)

(73) Assignee: Google, Inc., Mountain View, CA (US)

(*) Notice: Subject to any disclaimer, the term of this patent is extended or adjusted under 35 U.S.C. 154(b) by 203 days.

(21) Appl. No.: 14/181,086

(22) Filed: Feb. 14, 2014

(65) Prior Publication Data

US 2015/0234006 A1 Aug. 20, 2015

(51) Int. Cl.
*G01N 21/88* (2006.01)
*G01R 31/308* (2006.01)
*G02F 1/13* (2006.01)
*G01N 21/95* (2006.01)

(52) U.S. Cl.
CPC ............ *G01R 31/308* (2013.01); *G02F 1/1309* (2013.01); *G01N 2021/9513* (2013.01)

(58) Field of Classification Search
CPC .................................................... G02F 1/1309
See application file for complete search history.

(56) References Cited

U.S. PATENT DOCUMENTS

| | | | |
|---|---|---|---|
| 7,826,057 B2 | 11/2010 | Kim et al. | |
| 7,831,086 B2 * | 11/2010 | Kondo | G06T 3/0062 345/419 |
| 7,941,237 B2 | 5/2011 | Parker et al. | |
| 8,492,739 B2 | 7/2013 | Choi et al. | |
| 8,561,288 B2 | 10/2013 | Bawolek | |
| 2003/0215129 A1* | 11/2003 | Yang | G06T 7/0002 382/149 |
| 2005/0167620 A1* | 8/2005 | Cho | G01N 21/95 250/559.45 |
| 2008/0284455 A1* | 11/2008 | Obikane | G01R 31/2893 324/754.08 |
| 2010/0148083 A1* | 6/2010 | Brown | G01J 3/02 250/372 |
| 2013/0068368 A1 | 3/2013 | Kim et al. | |
| 2014/0009181 A1* | 1/2014 | Xue | G01R 31/312 324/754.03 |
| 2014/0295771 A1* | 10/2014 | Finlow-Bates | H04W 24/06 455/67.14 |

* cited by examiner

*Primary Examiner* — Tung X Nguyen
*Assistant Examiner* — Feba Pothen
(74) *Attorney, Agent, or Firm* — Blakely Sokoloff Taylor & Zafman LLP

(57) ABSTRACT

A test apparatus includes a display sled having a mount for holding a display under test ("DUT"). The display sled is supported by a frame and moves between a test position and a load position. A lamp source is supported by the frame and positioned to illuminate the DUT when the display sled is in the test position. A measurement camera is supported by the frame and positioned to capture one or more test images output by the DUT when the DUT is illuminated by the lamp source. Driver circuitry generates the one or more test images to drive the DUT. An electrical interconnect establishes an electrical connection between the driver circuitry and the DUT when the display sled is in the test position. An actuator is coupled to physically manipulate the electrical interconnect to engage or disengage the electrical connection between the driver circuitry and the DUT.

20 Claims, 5 Drawing Sheets

INSTRUMENT FOR AUTOMATED TESTING OF DISPLAYS

TECHNICAL FIELD

This disclosure relates generally to instruments for testing displays.

BACKGROUND INFORMATION

A liquid crystal displays ("LCD") is a well-known display technology. Unpolarized or linearly polarized light is incident on the LCD. A first polarizer polarizes the light. Liquid crystals inside the display rotate the polarization state of the light based on the voltage applied. A final output polarizer only transmits one polarization direction. Thus, the amount of polarization rotation modulates the brightness of the light to create the desired image. This is done using Malus' Law where $I=Io*cos^2(\theta)$. Io is the incident power, $\theta$ is the angle between the rotated light and the output polarizer, and I is the output power. Measuring the resulting image that goes to the observer is challenging in a test environment. The manufacturers of these parts use human operators with optical projectors to enlarge and assess the image performance from the LCD for these small display panels.

Liquid crystal on silicon ("LCOS") is a display technology that uses polarized light to create an image. As an example, when p-polarized light is used to illuminate an LCOS display, the LCOS changes the incident p-polarization into a reflected mix of p-polarization and s-polarization based on the desired pixel intensity. The s-polarized portion is transmitted to the user using a polarizing beam splitter ("PBS") while the p-polarized portion is thrown away. Again, measuring the resulting image that goes to the observer is challenging in a test environment. The manufacturers of these parts also use human operators with optical projectors to enlarge and assess the image performance from the LCOS.

BRIEF DESCRIPTION OF THE DRAWINGS

Non-limiting and non-exhaustive embodiments of the invention are described with reference to the following figures, wherein like reference numerals refer to like parts throughout the various views unless otherwise specified. The drawings are not necessarily to scale, emphasis instead being placed upon illustrating the principles being described.

DETAILED DESCRIPTION

Embodiments of a system, apparatus, and method of operation for automated measuring/testing of displays, such as microdisplays, are described herein. In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
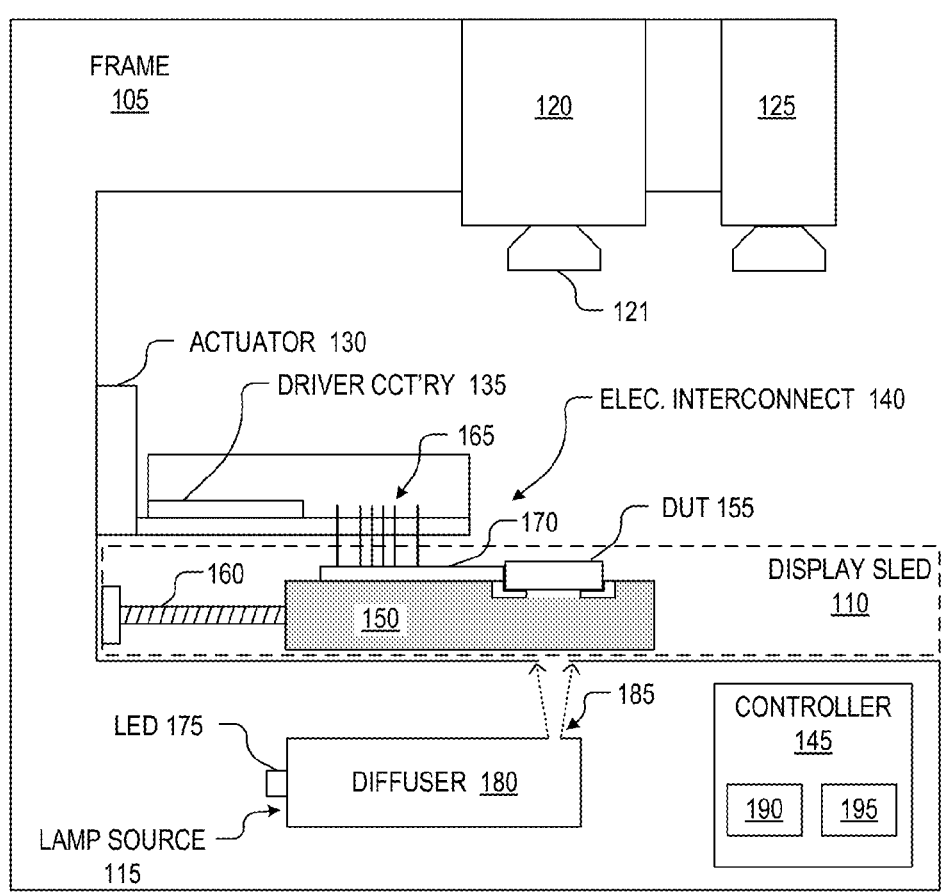
FIG. 1 is a block diagram illustrating an automated test instrument for testing the performance of emissive or transmissive displays, in accordance with an embodiment of the disclosure.

FIG. 1 is a block diagram illustrating an automated test instrument 100 for testing the performance of emissive or transmissive displays, in accordance with an embodiment of the disclosure. The illustrated embodiment of automated test instrument 100 includes a frame 105, a display sled 110, a lamp source 115, a measurement camera 120, an identification camera 125, an actuator 130, driver circuitry 135, an electrical interconnect 140, and a controller 145. The illustrated embodiment of display sled 110 includes a mount 150 for holding the display under test ("DUT") 155 and a sled actuator 160. The illustrated embodiment of electrical interconnect 140 includes terminals 165 and contact region 170. The illustrated embodiment of lamp source 115 includes a light emitting diode ("LED") 175 and diffuser 180 having an emission aperture 185. The illustrated embodiment of controller 145 includes logic 190 and memory 195.

Figure 5:
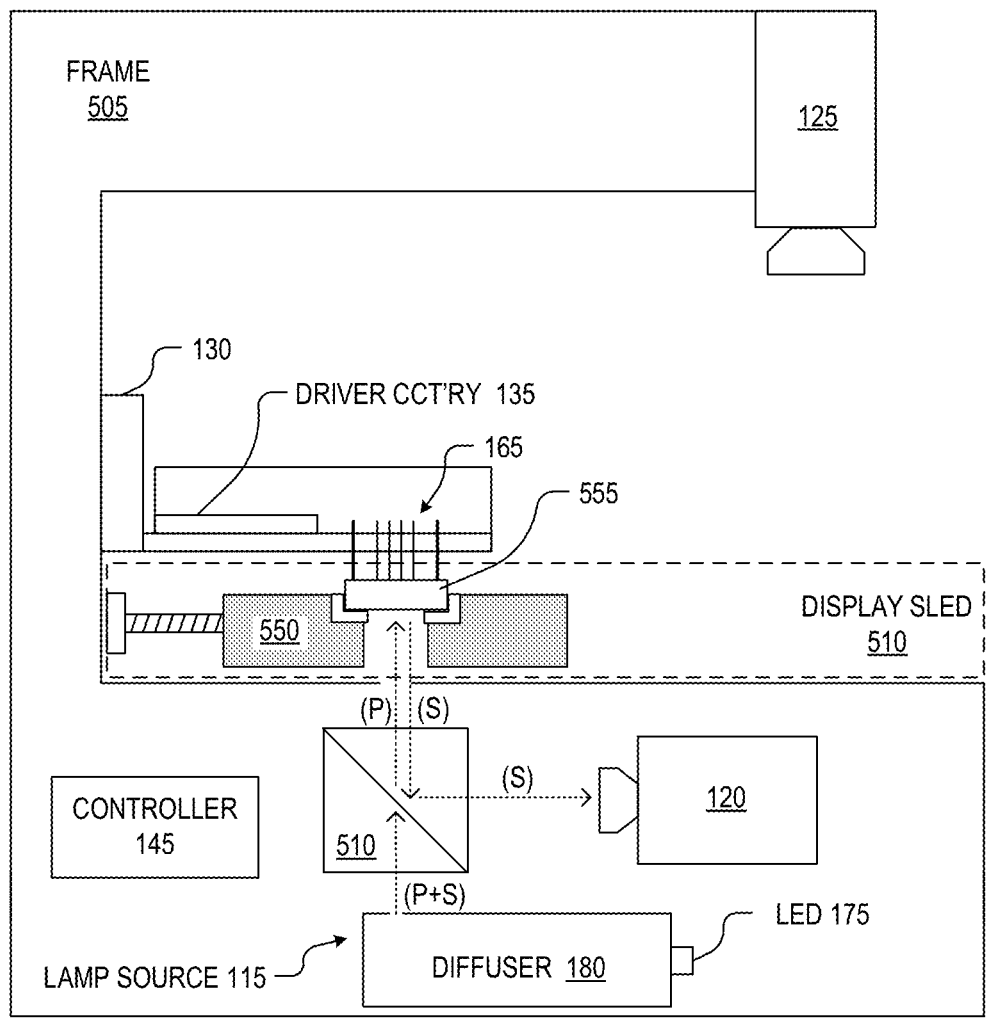
FIG. 5 is a block diagram illustrating an automated test instrument for testing the performance of a reflective display, such as a liquid crystal on silicon ("LCoS") display, in accordance with an embodiment of the disclosure.

Automated test instrument 100 is an apparatus for measuring and testing displays for faults. Such displays include microdisplays, such as transmissive displays (e.g., backlit LCD displays) or emissive displays (e.g., organic light emitting diode ("OLED") displays). Automated test instrument 100 eliminates subjective human judgment in the measurement process and provides rapid automated testing of one or more displays under test ("DUTs") 155. Automated test instrument 500, illustrated in FIG. 5, is similar to automated test instrument 100, as is discussed below, but is designed for testing reflective displays, such as a liquid crystal on silicon ("LCoS") display. Automated test instrument 500 is discussed in greater detail below in connection with FIG. 5.

Automated test instrument 100 is capable of performing multiple different types of test procedures on a given DUT 155. For example, DUT 155 may be driven with a reference test pattern or test image, the test image output by DUT 155 captured by measurement camera 120, and the captured test image analyzed by logic 190 of controller 145 to determine if DUT 155 has a failure. Determining whether DUT 155 has a failure may include comparing the capture test image against various threshold values, such as number of acceptable faulty pixels (e.g., 0, 1, 2, etc.), contrast levels, black levels, response time, color quality, etc. Any number of image analysis algorithms may be applied. In one embodiment, measurement camera 120 has sufficient resolution to identify a single faulty pixel on DUT 155. The test results may then be logged against an identifier for the given DUT 155 and stored into memory 195 for subsequent output. In one embodiment, test results include an itemization of failures on a per-pixel basis.

Figure 3A:
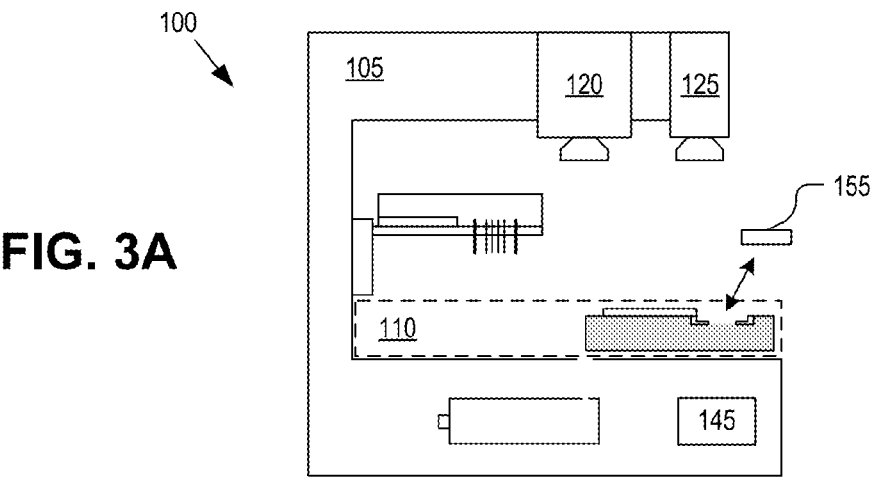
FIG. 3A illustrates loading/unloading a display into the automated test instrument, in accordance with an embodiment of the disclosure.
Figure 3B:
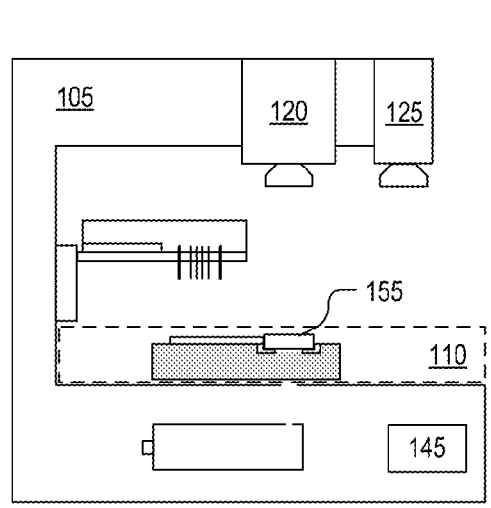
FIG. 3B illustrates a display that has been moved into a test position of the automated test instrument, in accordance with an embodiment of the disclosure.
Figure 3C:
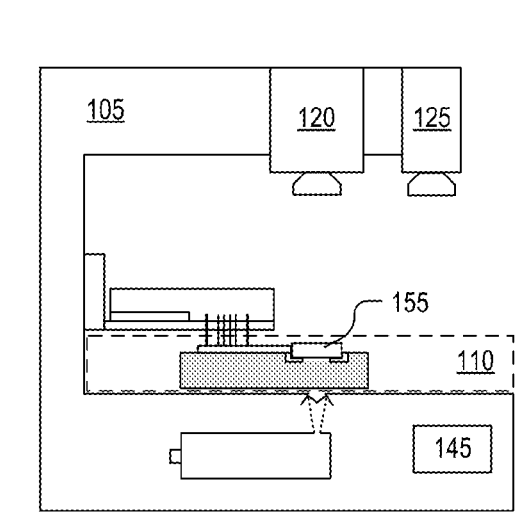
FIG. 3C illustrates how electrical connections to the display loaded into the automated test instrument are achieved, in accordance with an embodiment of the disclosure.

Automated test instrument 100 includes display sled 110, which moves between an load/unload position (e.g., see FIG. 3A) and a test position (e.g., see FIGS. 1 and 3B). This provides the operator easy access for loading the instrument with DUT 155 and is functional to accept different types of displays having different electrical interfaces. Display sled 110 includes mount 150, which is amenable to accepting and holding displays of different shapes and sizes. Display sled 110, along with mount 150, may translate or rotate between the load/unload position and the test position on a track, guide, hinge, or otherwise. In the illustrated embodiment, display sled 110 is translated between the two positions under the influence of sled actuator 160. Sled actuator 160 may be implemented using a variety of different actuating technologies including a screw drive, a belt system, an electro-magnetic actuator, a servo, or otherwise. In other embodiments, display sled 110 may be physically manipulated between the load/unload position and the test position by the operator.

Once in the test position, DUT 155 may be driven with one or more test images by driver circuitry 135. Driver circuitry 135 may include a video chip or rendering circuitry to generate the test images and provide operational power and control signals to DUT 155. Electrical connections are established between driver circuitry 135 and DUT 155 via electrical interconnect 140 in concert with actuator 130. Electrical interconnect 140 includes terminals 165 that make physical and electrical contact with contacts on contact region 170 disposed on display sled 110. Actuator 130 physically manipulates terminals 165 to engage contact region 170 once display sled 110 is moved to the test position. In the illustrated embodiment, terminals 165 are translated along a first axis that is orthogonal to a second axis along which display sled 110 is translated.

Actuator 130 may be implemented using a variety of actuating technologies including servos, electro-mechanical motors, electro-static actuator, micro-electro-mechanical actuators, or otherwise. In one embodiment, terminals 165 may be implemented using pogo pins that align with contact pads coupled to a flex ribbon used to implement contact region 170. Of course, other physical interconnect elements and geometries may be implemented. Similarly, other orientations and configurations for actuating electrical interconnect 140 to engage/disengage an electrical connection with DUT 155 may be implemented as well.

In the illustrated embodiment, lamp source 115 is disposed below display sled 110 to illuminate DUT 155 from its backside such that DUT 155 outputs a test image to measurement camera 120 disposed above display sled 110. Lamp source 115 may be implemented using a variety of lamp technologies includes LEDs, fluorescent lights, halogen lights, or otherwise. Lamp source 115 may be a monochromatic light source, a multi-color light source, a broadband light source, or otherwise. In the illustrated embodiment, lamp source 115 includes an LED 175 that launches lamp light into a diffuser 180. Diffuser 180 includes a cavity with diffuse inner sides walls that homogenize the lamp light and emit the lamp light through an emission aperture 185 aligned with DUT 155. In one embodiment, lamp source 115 further includes a polarizer for generating polarized light.

In the illustrated embodiment, measurement camera 120 is disposed above DUT 155 to capture the test image output from DUT 155 when display sled 110 is in the test position. Measurement camera 120 may be implemented using various camera technologies (e.g., CMOS or CCD cameras), and in at least some embodiments, have a resolution sufficient to identify a single faulty pixel or multiple pixel failures on a per pixel basis.

In the illustrated embodiment, camera module 120 includes a lens assembly 121 for focusing on DUT 155. Lens assembly 121 may be implemented as a telecentric lens while measurement camera 120 may be provided with an offset adjustment (e.g., vertical adjustment). A telecentric lens maintains a constant magnification despite various offsets between lens assembly 121 and DUT 155. This accommodates different DUT 155 form factors having the same display size. The vertical offset adjustment facilities bring the captured test image into focus for different DUT 155 form factors. Alternatively, lens assembly 121 may be implemented with a variable focus lens (e.g., autofocus lens) and used in connection with feature detection and size correlation logic within controller 145 or measurement camera 120. Again, the variable focus lens facilitates different size and form factors for DUT 155.

Code camera 125 is provided in automated test instrument 100 to enable an auto identification feature. Code camera 125 may be implemented with a conventional CCD or CMOS image sensor, a barcode scanner, or otherwise. Code camera 125 operates to read identifying marks on DUT 155 (e.g., a bar code, product code, serial number, etc.). This information may be used to identify the particular type of DUT 155, select appropriate test procedures from a catalog of test procedures (e.g., test images), and index the test results with an identifier for output or storing to memory 195.

Controller 145 is coupled to the various operational components of automated test instrument 100 to control and synchronize their operation in an automated manner. Controller 145 includes logic 190 that controls the operational phases of display sled 110, lamp source 115, actuator 130, driver circuitry 135, measurement camera 120, and code camera 125. Logic 190 may be implemented has hardware logic (e.g., application specific integrated circuit, field programmable gate array, or otherwise), software logic/instructions executed on a micro-processor, or a combination of both. Memory 195 may include volatile and/non-volatile memory. Although not illustrated, controller 145 may further include various input/output ports and interfaces for receiving user inputs and outputting user prompts and test results.

Figure 2:
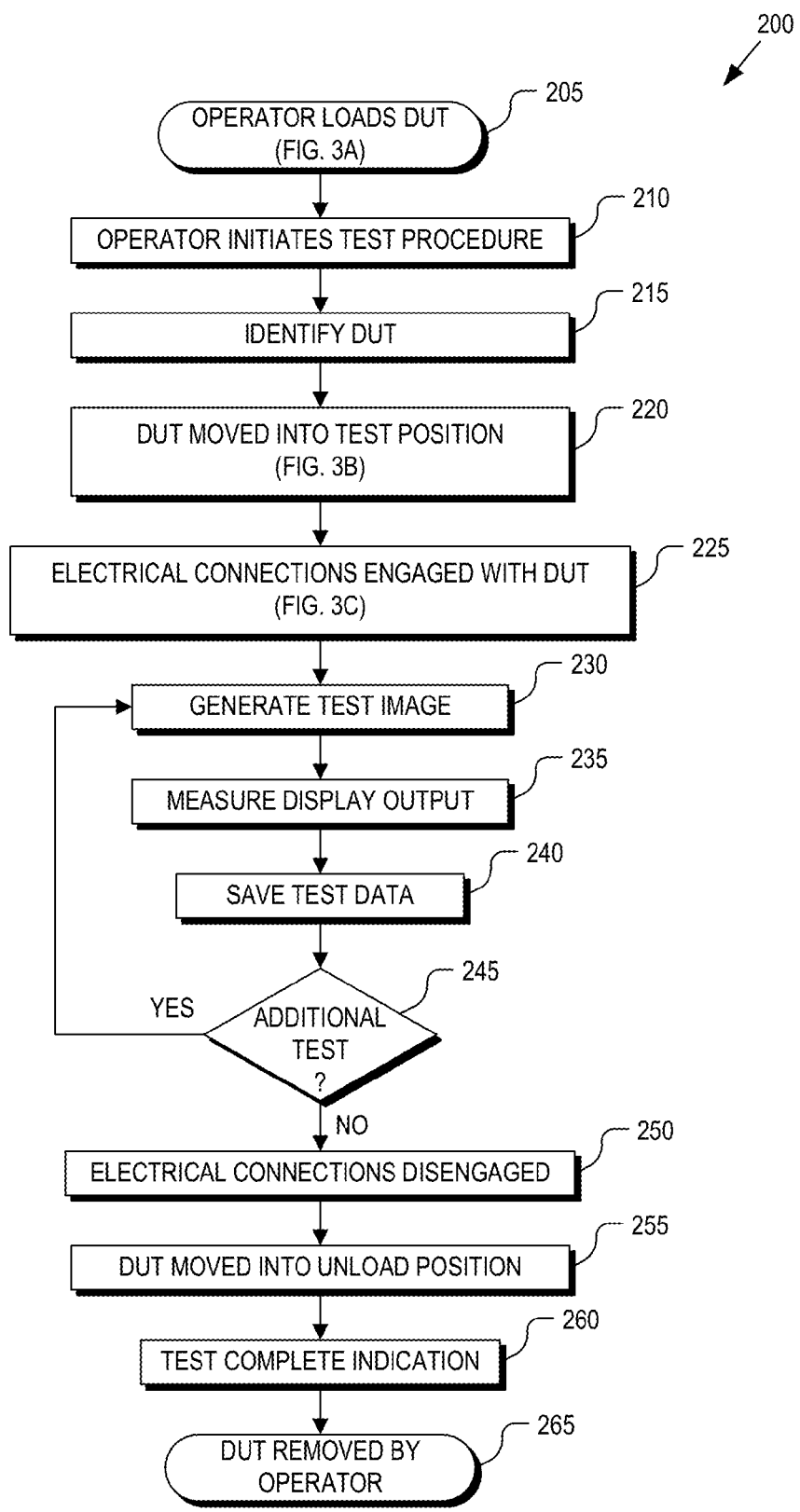
FIG. 2 is a flow chart illustrating operation of an automated test instrument for testing the performance of displays, in accordance with an embodiment of the disclosure.

FIG. 2 is a flow chart illustrating a process 200 of operating automated test instrument 100 for testing the performance of DUT 155, in accordance with an embodiment of the disclosure. Process 200 is described with reference to FIGS. 1, 3A, 3B, and 3C. The order in which some or all of the process blocks appear in process 200 should not be deemed limiting. Rather, one of ordinary skill in the art having the benefit of the present disclosure will understand that some of the process blocks may be executed in a variety of orders not illustrated, or even in parallel.

In a process block 205, an operator loads DUT 155 into mount 150 of display sled 110 (see FIG. 3A). When inserting DUT 155 into automated test instrument 100, display sled 110 is moved to the load/unload position, as illustrated in FIG. 3A. Mount 150 may include a friction fit, adjustable clamps, or otherwise that hold DUT 155 temporarily and securely in place. Once loaded, the operator initiates a test procedure with a user input selection (process block 210). In one embodiment, the user input may be solicited and received from a user interface (e.g., button, externally coupled computer, etc.) communicatively coupled to controller 145.

Once a test procedure has been initiated, automated test instrument 100 identifies the specific DUT 155 loaded into display sled 110 using code camera 125. In a process block 215, display sled 110 moves DUT 155 into optical aligned with code camera 125 where code camera 125 reads an identifying code physically printed on DUT 155. The identifying code may be a barcode, a serial number, a product number, or various other marks. In various embodiments, code camera 125 may acquire an image of a mark on DUT 155 or an image of DUT 155 itself, and character recognition or image recognition techniques used to identify the type of display that is DUT 155. For example, controller 145 may use the identifying marks to determine the particular model of display as well as whether the display is transmissive, reflective, or emissive. If DUT 155 is determined to be transmissive or reflective, then lamp source 115 will be enabled as a source of lamp light. If DUT 155 is determined to be emissive, then external lamp light is not necessary and lamp source 115 remains disabled.

In a process block 220 (see FIG. 3B), display sled 110 moves DUT 155 into the test position where DUT 155 is optically aligned with measurement camera 120 and lamp source 115. Once in the test position, electrical connections are established between driver circuitry 135 and DUT 155 (process block 225; see FIG. 3C). In the illustrated embodiment, controller 145 causes actuator 130 to move terminals 165 vertically down and engage contact region 170.

Once an electrical connection is established between driver circuitry 135 and DUT 155, controller 145 enables driver circuitry 135. Driver circuitry 135 both powers DUT 155 and drives DUT 155 with one or more test images (process block 230). For example, a test image may be an all-black image to identify failed pixels in the case of a backlit LCD display, an all red, green, or blue image to identify failed pixels in the case of emissive displays, images with regular patterns, grey scale images, or otherwise. Each test image is captured by measurement camera 120 and analyzed by logic 190 of controller 145 (process block 235). The analysis identifies a faulty pixel when a given pixel fails to satisfy a specified threshold level. Faulty pixels or other system level faults with DUT 155 are reported and saved into memory 195 as test results indexed to an identifier or part number for DUT 155 (process block 240).

If a given DUT 155 is to be driven with multiple different test images (decision block 245), then process 200 loops back to process block 230 and repeats until all test images have been acquired and analyzed. In a process block 250, the electrical connection between driver circuitry 135 and DUT 155 is disengaged. In the illustrated embodiment, actuator 130 raises terminals 165 to disengage the electrical connection under the influence of controller 145. After disengaging the electrical connections, display sled 110 moves DUT 155 to the load/unload position (process block 255; see FIG. 3A) and automated test instrument 100 notifies the operator that the test procedure is complete (process block 260). Finally, in a process block 265, the operator removes DUT 155 from mount 150 of display sled 110. In alternative embodiments (not illustrated), loading and unloading DUT 155 may also be automated.

Figure 4:
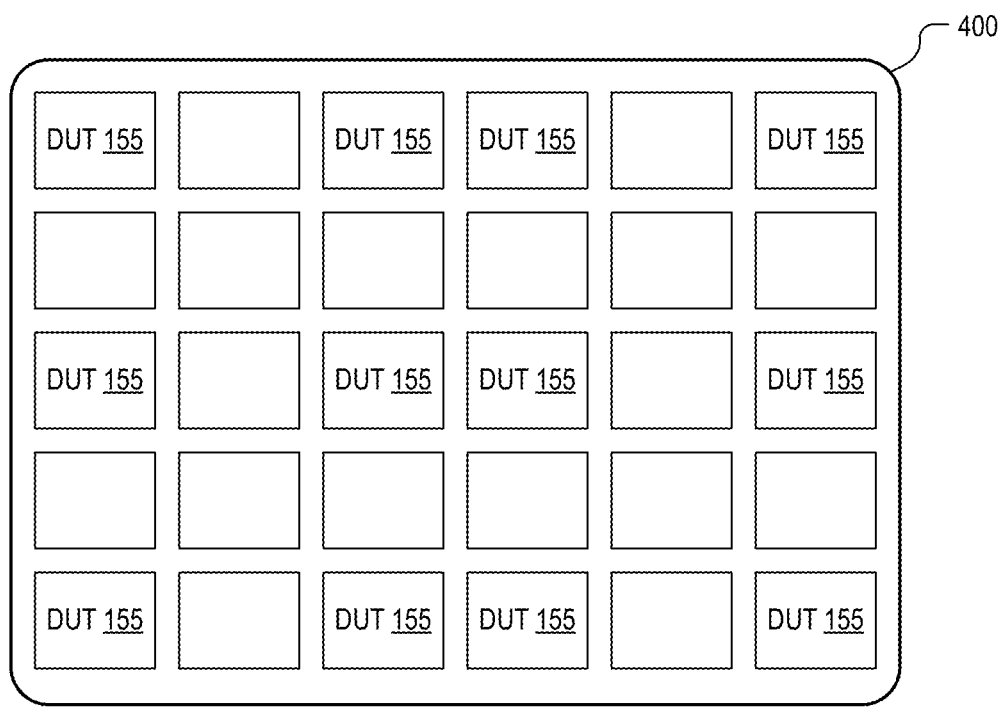
FIG. 4 illustrates a tray for holding multiple displays for successive testing in an automated test instrument, in accordance with an embodiment of the disclosure.

FIG. 4 illustrates a tray 400 for holding multiple DUTs 155 for successive testing in automated test instrument 100, in accordance with an embodiment of the disclosure. Mount 150 of display sled 110 may be modified and enlarged to support a larger tray 400 capable of holding many DUTs 155 for rapid batch testing. Although not illustrated, tray 400 may include contact regions associated with each cradle area on tray 400 for holding a separate DUT 155. These on-tray contact regions may then be engaged by terminals 165 to establish an electrical connection to a given DUT 155. During operation, a user would load up tray 400 with a batch of DUTs 155 and automated test instrument 100 would successively execute the test procedure described in connection with FIG. 2 for each DUT 155 loaded into tray 400. In one embodiment, display sled 110 would be capable to translation along two orthogonal axes to successively align each DUT 155 into the test position. In one embodiment, the test results are also batch reported into memory 195 for operator readout or output from the automated test instrument 100.

FIG. 5 is a block diagram illustrating an automated test instrument 500 for testing the performance of a reflective display or reflective DUT 555, in accordance with an embodiment of the disclosure. An example of a reflective display is a liquid crystal on silicon ("LCoS") display. Automated test instrument 500 is similar to automated test instrument 100 with at least the differences enumerated below and operates using a similar process as described in connection with FIG. 2.

The illustrated embodiment of automated test instrument 500 includes a frame 505 that supports measurement camera 120 below display sled 510, as opposed to above. A polarizing beam splitter ("PBS") cube 510 is also included below display sled 510 and optically aligned under DUT 555 when display sled 510 is moved into the test position. During operation, lamp source 115 outputs lamp light, which can be either non-polarized light (including P & S polarizations) or polarized light (P polarized). P-polarized light passes through PBS cube 510 and illuminates DUT 555. The operation of LCoS displays is well known. DUT 555 changes the incident p-polarization into a reflected mix of p-polarization and s-polarization based on the test image driven to the DUT 555. PBS cube 510 reflects the s-polarization, which represents the output test image, back to measurement camera 120 where it is captured for analysis by controller 145. Mount 550 of display sled 510 may be modified relative to mount 150 to accommodate the unique form factor of reflective displays and the fact that measurement camera 120 is disposed below display sled 510.

It should be appreciated that it is contemplated that in various other embodiments (not illustrated) the various functional components of both automated test instruments 100 and 500 may be rearranged into other geometries and relative positions, while still achieving the same overall functions described herein.

The processes explained above are described in terms of computer software and hardware. The techniques described may constitute machine-executable instructions embodied within a tangible or non-transitory machine (e.g., computer) readable storage medium, that when executed by a machine will cause the machine to perform the operations described. Additionally, the processes may be embodied within hardware, such as an application specific integrated circuit ("ASIC") or otherwise.

A tangible machine-readable storage medium includes any mechanism that provides (i.e., stores) information in a non-transitory form accessible by a machine (e.g., a computer, network device, personal digital assistant, manufacturing tool, any device with a set of one or more processors, etc.). For example, a machine-readable storage medium includes recordable/non-recordable media (e.g., read only memory (ROM), random access memory (RAM), magnetic disk storage media, optical storage media, flash memory devices, etc.).

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An apparatus for testing displays, comprising:
   a frame;
   a display sled including a mount for holding a display under test ("DUT"), wherein the display sled is supported by the frame;
   a first actuator to move the display sled between a test position and a load position, wherein the display sled to receive the DUT while the display sled is in the load position, wherein the DUT electrically couples to contacts of a contact region disposed on the display sled;
   a lamp source supported by the frame and positioned to illuminate the DUT when the display sled is in the test position;
   a measurement camera supported by the frame and positioned to capture one or more test images output by the DUT when the DUT is illuminated by the lamp source;
   driver circuitry to generate the one or more test images to drive the DUT, wherein the first actuator to move the display sled between the test position and the load position includes the first actuator to translate the display sled along a first axis, wherein movement of the display sled along the first axis moves both the DUT and the contact region relative to the lamp source, the measurement camera and the driver circuitry, and moves the DUT into optical alignment with the measurement camera and with the lamp source when the display sled is in the test position;
   an electrical interconnect to temporarily establish an electrical connection between the driver circuitry and the DUT via the contacts of the contact region when the display sled is in the test position; and
   a second actuator coupled to physically manipulate the electrical interconnect to engage or disengage the electrical connection between the driver circuitry and the DUT.

2. The apparatus of claim 1, further comprising:
   a controller including operational logic and memory, wherein the controller is coupled to automate operation of at least the driver circuitry, the measurement camera, and the second actuator to acquire the one or more test images output from the DUT and to store test results in the memory indicative of an operational performance of the DUT.

3. The apparatus of claim 2, further comprising:
   an identification camera positioned to capture a code image of a code disposed on the DUT, wherein the controller is coupled to store an identifier generated based on the code image indexed to the test results in the memory.

4. The apparatus of claim 3, wherein the controller includes logic that enables the lamp source when the DUT is determined, based upon the code image, to be one of a transmissive or reflective display and wherein the controller includes logic that disables the lamp source when the DUT is determined, based upon the code image, to be an emissive display.

5. The apparatus of claim 3, wherein the identification camera and the measurement camera are supported by the frame above the display sled and the lamp source is supported by the frame below the display sled.

6. The apparatus of claim 3, wherein the measurement camera is supported by the frame below the display sled, the apparatus further comprising:
   a polarizing beam splitter ("PBS") disposed below the display sled, wherein the PBS is positioned to pass light emitted from the lamp source as polarized light to the DUT and positioned to reflect the one or more test images output from the DUT to the measurement camera.

7. The apparatus of claim 1, wherein the lamp source comprises a light emitting diode ("LED") and a diffuser having an emission aperture aligned to illuminate the DUT when the display sled is in the test position.

8. The apparatus of claim 1, wherein movement of the display sled along the first axis further aligns the contacts of the contact region with terminals of the electrical interconnect when the display sled is in the test position, wherein the second actuator translates the terminals of the electrical interconnect relative to the contacts of the contact region in response to movement of the display sled into the test position.

9. The apparatus of claim 8, wherein the second actuator translates the terminals along a second axis that is orthogonal to the first axis.

10. The apparatus of claim 2, further comprising:
    a tray for holding a plurality of DUTs in a pattern, wherein the tray is mountable to the display sled, wherein the first actuator includes a sled actuator coupled to the display sled to translate the display sled along two orthogonal directions, wherein the controller include logic to successively drive each of the plurality of DUTs with the one or more test images and to store a plurality of sets of test results in the memory to automate batch testing of the plurality of DUTs.

11. The apparatus of claim 2, wherein the measurement camera has sufficient resolution to identify a failure of a single pixel in the DUT.

12. The apparatus of claim 2, wherein the measurement camera is mounted with a translation adjustment to adjust an offset between the measurement camera and the DUT and the measurement camera includes a telecentric lens.

13. An automated method for testing one or more displays, the method comprising:
    moving a display sled of a test instrument from a load position to a test position after a display under test ("DUT") has been inserted into a mount on the display sled, wherein the DUT, while in the mount, is electrically coupled to contacts of a contact region disposed on the display sled, wherein moving the display sled from the load position to the test position includes translating the display sled along a first axis, wherein translating the display sled along the first axis moves both the DUT and the contact region relative to a lamp source, a measurement camera and driver circuitry of the test instrument, and moves the DUT into optical alignment with the measurement camera and with the lamp source when the display sled is in the test position;
    determining if the DUT requires external illumination for operation, and if so, illuminating the DUT with the lamp source when the sled is in the test position;

after the display sled moves to the test position, establishing, via the contacts, an electrical connection between the DUT and the driver circuitry;

with the driver circuitry, driving the DUT to emit one or more test images;

capturing the one or more test images emitted from the DUT with the measurement camera; and analyzing the test images captured by the measurement camera of the test instrument with a controller to determine whether the DUT has one or more faults.

14. The automated method of claim 13, further comprising:
acquiring a code image of a code disposed on the DUT with an identification camera of the test instrument.

15. The automated method of claim 14, wherein the determining if the DUT requires external illumination for operation is determined based upon the code image acquired with the identification camera.

16. The automated method of claim 15, wherein the identification camera and the measurement camera are supported by a frame of the test instrument above the display sled and the lamp source is supported by the frame below the display sled.

17. The automated method of claim 15, wherein the measurement camera is supported by a frame of the test instrument below the display sled, the automated method further comprising:

polarizing light emitted from the lamp source with a polarizing beam splitter disposed between the lamp source and the display sled to emit polarized light; and reflecting the one or more test images output from the DUT towards the measurement camera, wherein the DUT comprises a reflective display.

18. The automated method of claim 13, wherein the lamp source comprises a light emitting diode ("LED") and a diffuser having an emission aperture aligned to illuminate the DUT when the display sled is in the test position.

19. The automated method of claim 13, wherein translating the display sled along the first axis aligns the contacts of the contact region with terminals of an electrical interconnect of the test instrument when the display sled is in the test position, wherein establishing the electrical connection between the DUT and the driver circuitry comprises translating the terminals relative to the contacts in response to movement of the display sled into the test position.

20. The automated method of claim 13, further comprising:
moving the display sled from the load position to the test position after a plurality of DUTs in a tray have been mounted on the display sled;

successively moving the tray to align each of the plurality of DUTs with the measurement camera;

capturing one or more test images from each of the plurality of DUTs; and determining whether any of the plurality of DUTs are faulty based upon the one or more test images captured for each of the plurality of DUTs.

* * * * *